United States Patent
Segovia Martinez

(10) Patent No.: US 9,844,671 B2
(45) Date of Patent: Dec. 19, 2017

(54) COCHLEAR IMPLANT AND AN OPERATING METHOD THEREOF

(71) Applicant: Oticon Medical A/S, Smørum (DK)

(72) Inventor: Manuel Segovia Martinez, Smørum (DK)

(73) Assignee: Oticon Medical A/S, Smørum (DK)

( * ) Notice: Subject to any disclaimer, the term of this patent is extended or adjusted under 35 U.S.C. 154(b) by 0 days.

(21) Appl. No.: 14/991,319

(22) Filed: Jan. 8, 2016

(65) Prior Publication Data

US 2016/0199643 A1 Jul. 14, 2016

(30) Foreign Application Priority Data

Jan. 13, 2015 (EP) .................................... 15150887

(51) Int. Cl.
| | |
|---|---|
| *A61N 1/36* | (2006.01) |
| *A61N 1/05* | (2006.01) |
| *H03G 9/02* | (2006.01) |
| *H04R 25/00* | (2006.01) |

(52) U.S. Cl.
CPC ....... *A61N 1/36032* (2013.01); *A61N 1/0541* (2013.01); *A61N 1/36038* (2017.08); *H03G 9/025* (2013.01); *H04R 25/606* (2013.01)

(58) Field of Classification Search
CPC ................................................. A61N 1/36032
USPC .............................................. 607/55–57, 137
See application file for complete search history.

(56) References Cited

U.S. PATENT DOCUMENTS

| | | | |
|---|---|---|---|
| 4,207,441 A | 6/1980 | Ricard et al. | |
| 4,532,930 A | 8/1985 | Crosby et al. | |
| 5,832,444 A | 11/1998 | Schmidt | |
| 6,097,824 A | 8/2000 | Lindemann et al. | |
| 2002/0076072 A1 | 6/2002 | Cornelisse | |
| 2007/0016267 A1* | 1/2007 | Griffin | H04R 25/505 607/57 |
| 2012/0008809 A1* | 1/2012 | Vandali | A61N 1/36032 381/317 |
| 2012/0109006 A1* | 5/2012 | James | A61N 1/36032 600/559 |
| 2013/0103396 A1 | 4/2013 | Swanson et al. | |
| 2014/0074463 A1 | 3/2014 | Litvak et al. | |
| 2014/0198922 A1 | 7/2014 | Mauger et al. | |

(Continued)

*Primary Examiner* — Allen Porter, Jr.
(74) *Attorney, Agent, or Firm* — Birch, Stewart, Kolasch & Birch, LLP

(57) ABSTRACT

A cochlear implant is disclosed in an embodiment. The implant includes a signal level detector configured to determine a total signal level of an incoming acoustic signal and a processing unit configured to determine, in accordance with the determined total signal level, an intermediate knee point for each of a plurality of frequency bands. The implant includes a bandpass filters configured to generate a plurality of band limited audio signals in dependence upon the incoming acoustic signal, each band limited acoustic signal representing an associated audio frequency range relating to at least one electrode of a plurality of an implanted electrode array of the cochlear implant. The implant includes a pulse controller configured to deliver electrical stimulation signals to the plurality of electrodes of the implanted electrode array based on the generated signals and the determined intermediate knee point corresponding to the frequency range.

18 Claims, 5 Drawing Sheets

(56) References Cited

U.S. PATENT DOCUMENTS

2015/0016647 A1\* 1/2015 Segovia Martinez . H04R 3/002
  381/317

\* cited by examiner

COCHLEAR IMPLANT AND AN OPERATING METHOD THEREOF

FIELD

The disclosure relates to a cochlear implant and a method for operating the cochlear implant adapted to electrically stimulate the auditory nerve. In particular, the disclosure relates to signal processing and stimulation strategies used by the cochlear implant.

BACKGROUND

Sensorineural type of hearing loss is due to the absence or the destruction of the hair cells in the cochlea, which are needed to convert acoustic signals into auditory nerve impulses. People suffering from such type of loss are unable to derive any benefit from conventional hearing aid systems. This is because their mechanism for converting sound energy into auditory nerve impulses has been damaged or substantially damaged.

To overcome sensorineural deafness, numerous Implantable Cochlear Stimulation (ICS) systems—or cochlear prosthesis/implant—have been developed which seek to bypass the hair cells in the cochlea by presenting electrical stimuli directly to the auditory nerve fibers, leading to the perception of sound in the brain and at least a partial restoration of hearing function. The common denominators in most of these cochlear implants have been the implantation of electrodes into the cochlea, and a suitable external source of an electrical signal for the electrodes.

In order to effectively stimulate the nerve cells, the electronic circuitry and the electrode array of the cochlear prosthesis perform the function of separating the acoustic signal into a number of channels of information, each representing the intensity of a narrow frequency range within the acoustic spectrum. Ideally, the electrode array would convey each channel of information selectively to the subset of auditory nerve cells. The nerve cells are arranged in an orderly tonotopic sequence, from high frequencies at the basal end of the cochlear spiral to progressively lower frequencies towards the apex, and ideally the entire length of the cochlea would be stimulated by electrode array implanted in the cochlea to provide a full or substantially full frequency range of hearing.

The signal provided to the electrode array is generated by a signal processing component of the Implantable Cochlear Stimulation (ICS) system. An incoming acoustic signal is processed by a family of bandpass filters. Then, the output of each bandpass filter is independently amplitude mapped into a simulation level, using a mapping consistent with normal perception. However, conventional techniques do not provide for an adaptive mapping.

There is a need to offer an improved experience to a cochlear implant user by utilizing a mapping technique that automatically adapts in accordance with the environment of the user such that realistic mapping of overall loudness of sound from the acoustic domain to the electrical stimulation domain is maintained.

SUMMARY

As an illustration, the cochlear implant is defined to typically include i) an external part including an input transducer for receiving an incoming acoustic signal from a user's surroundings and providing a corresponding electric input signal, a signal processing circuit for processing the electric input signal and for determining sequences of pulses for stimulation of the electrodes in dependence on the processed incoming acoustic signal, ii) a (typically wireless, e.g. inductive) communication link for simultaneously transmitting information about the stimulation sequences and for transferring energy to iii) an implanted part allowing the stimulation to be generated and applied to a number of electrodes, which are implantable in different locations of the cochlea allowing a stimulation of one or more hearing nerves in different frequencies of the audible range. Such systems are e.g. described in U.S. Pat. No. 4,207,441 and in U.S. Pat. No. 4,532,930. It would be apparent that the disclosure is applicable to other partially or completely implanted cochlear implant system as well.

The cochlear implant may include a single unit or several units, such as in a bilateral cochlear implant system, that communicating electronically with each other.

The disclosure provides for a transfer (mapping) function where the acoustic energy, represented by signal level, as received on the input transducers on logarithmic scale are mapped directly to the electrical stimulation levels. In other words, the mapping function defines how target charge amounts for individual charge pulse in each pulse stream or auditory channel associated with the implanted electrodes may be computed from the levels of the input signal using linear or piecewise linear mapping function. Typically, the mapping function extends linearly between a lower kneepoint and an upper kneepoint. In the lower knee point, the mapping function maps a lower threshold level $L_T$ corresponding to the user's hearing threshold into the threshold charge T. In the upper knee point, the mapping function maps a maximum comfortable level/upper threshold level $L_C$ corresponding to the user's UCL into the maximum comfortable charge C. Between the lower and upper knee points, the mapping function has a constant and positive incremental gain $G_i$ of $(C-T)/(L_C-L_T)$.

In one embodiment, an enhanced mapping function is disclosed. The enhanced mapping function deviates from the mapping function only in that it extends from the lower knee point to the upper knee point via an intermediate knee point, such that the incremental gain $G_i$ is larger between the lower knee point and the intermediate knee point than the incremental gain between the intermediate knee point and the upper knee point. At the intermediate knee point, the enhanced mapping function maps an intermediate threshold level to an intermediate charge. Compared to the mapping function, the enhanced mapping function thus applies a level expansion to audible signal levels below the intermediate threshold level and a level compression to comfortable signal levels above the intermediate threshold level. The purpose of the intermediate knee point is primarily to enhance information conveyed in speech and thus improve the user's ability to decode and understand speech. In an embodiment, the disclosure describes automatic determination and control of the intermediate kneepoint, as described below.

According to an embodiment, a cochlear implant is disclosed. The cochlear implant includes a signal level detector configured to determine a total signal level of an incoming acoustic signal and a processing unit configured to determine, in accordance with the determined total signal level, an intermediate knee point for each of a plurality of frequency bands. The cochlear implant further includes a bandpass filters configured to generate a plurality of band limited audio signals in dependence upon the incoming acoustic signal, each band limited acoustic signal representing an associated audio frequency range relating to at least one electrode of a plurality of an implanted electrode array of the cochlear implant. The cochlear implant also includes a pulse controller configured to deliver electrical stimulation signals to the plurality of electrodes of the implanted electrode array based on the generated band limited audio signals and the determined intermediate knee point corresponding to the frequency range.

This allows for automatically adapting electrical stimulation signals in accordance with the user's speech environment, which is classified based on the determined total signal level.

Hence, utilizing the disclosed dynamic mapping technique offers the cochlear implant user with an improved experience where realistic mapping of overall loudness of sound from the acoustic domain to the electrical stimulation domain is maintained.

In some embodiment, the input transducer may include multiple input transducer as an array, e.g. for providing direction-dependent audio signal processing in different beamforming modes. Beamforming involves processing audio signals received at the input transducers of the array in such a way as to make the array act as a highly directional microphone. In other words, beamforming provides a "listening beam" which points to, and receives, a particular sound source while attenuating other sounds and noise, including, for example, reflections, reverberations, interference, and sounds or noise coming from other directions or points outside the primary beam. Pointing such beams is typically referred as beamsteering and may be defined differently for different beamforming modes such as omnidirectional, high frequency directional, directional, etc.

In an embodiment, the signal level detector is configured to determine the total signal level by estimating signal levels obtained from at least one beamforming mode. Preferably, the total signal level is determined by performing weighted combination, such as weighted linear combination, of the estimated signal levels obtained from different beamforming modes if more than one beamforming mode is used. In other embodiments, other known methods for determining level may also be utilized.

As an illustrative example, known signal levels from different beamforming modes running in parallel such as Omnidirectional, HF Directional and Directional are utilized. The total signal level may be calculated using the coefficients for each mode as follows:

$$lvl_a = \alpha \cdot lvl_{omni} + \beta \cdot lvl_{HF\text{-}dir} + \gamma \cdot lvl_{dir}$$

where $lvl_a$ represents the total signal level, $lvl_{omni}$ represents signal level in omnidirectional mode, $lvl_{HF\text{-}dir}$ represents signal level in the HF-Directional mode, $lvl_{dir}$ represents signal level in the Directional mode and $\alpha$, $\beta$, and $\gamma$ represent linear percentage used by the beamforming of each beamforming mode at a given moment. The beamforming combines linearly a percentage of each mode. For example 30% omni and 70% Hf, then alpha=0.3, beta=0.7 and gamma=0. The percentages may either be pre-defined for different scenarios or may adaptively be calculated based on the value of the level estimate obtained from each of the beamforming modes.

Utilizing the above combination of level estimation with beamforming offers several advantages. Firstly, the intermediate kneepoint follows synchronously the beamforming level estimations. Secondly, when there is a change on the beamforming mode, the intermediate kneepoint modifications reduces the sensation of drastic loudness changes to the user of the cochlear implant. It would be apparent to the skilled person that instead of utilizing preferred beamforming based level estimation; other level estimation techniques to determine the total signal level may also be employed.

Thus, the input transducer is configured to receive the incoming acoustic signal and to provide a corresponding electric input signal. The cochlear implant may further includes a digitiser adapted to digitize the electric input signal and to provide the digitised signal as the input audio signal to a signal level detector for determining a total signal level.

The processing unit may also be configured to access a look up table. The look up table includes the predefined kneepoint values corresponding to each of the plurality of frequency bands (as illustrated below by an example) and a plurality of average signal levels (usually defining different speech situations). The predefined kneepoint values i.e. the predefined intermediate threshold levels relating to each frequency band, such as 57 dB SPL for frequency band 1500 Hz to 3450 Hz in medium speech situation (Refer Table 1 below), is used to make an interpolation for determining the intermediate kneepoint for the frequency band for a specific speech situation. The look up table is typically designed to maximize the speech information sent to the user while assuring comfort in noisy and loud conditions. The predefined kneepoint values are usually statistically determined in order to preserve a high percentage, such as at least 80%, 85%, 90% or 95%, of the speech information in different speech situations. Other percentage values are also within the scope of this disclosure. These speech situations may be identified to include quiet (average speech 60 dB SPL), medium (average speech 70 dB SPL) and loud environments (average speech 80 dB SPL).

The predefined intermediate threshold level kneepoint for each frequency band and each speech situation is obtained using a large database of speech signal from a specific language or similar languages. Similarly, the plurality of frequency bands may also be predefined, typically based on utilizing a large database of speech signal from a specific language or similar languages. For example, following frequency bands are defined using a database of speech signal from western languages—200 Hz to 850 Hz, 850 Hz to 1500 Hz, 1500 Hz to 3450 Hz, and 3450 Hz to 8000 Hz. The skilled person would appreciate that the numbers and width covered in the frequency bands and/or the speech situation condition and/or predefined kneepoint values may be varied, e.g. for other languages and for different users.

An illustrative look up table is included below, showing the relationship between the frequency bands, speech situations and intermediate threshold level kneepoints for western languages such as French Language.

TABLE 1

Look Up table defining intermediate kneepoints for each frequency band for different speech situations

| | Average Level (all bands) | | |
|---|---|---|---|
| Band (Hz) | 60 dB SPL Quiet (dB SPL) | 70 dB SPL Medium (dB SPL) | 80 dB SPL Strong (dB SPL) |
| 200 Hz to 850 Hz | 52 | 61 | 70 |
| 850 Hz to 1500 Hz | 52 | 61 | 70 |
| 1500 Hz to 3450 Hz | 47 | 57 | 66 |
| 3450 Hz to 8000 Hz | 41 | 50 | 58 |

The processing unit may be configured to determine the intermediate knee point by interpolating, such as linearly interpolating, predefined kneepoint values for each of the plurality of frequency bands. For example, if the total signal level is at 65 dB SPL, then the intermediate kneepoint will be between 52 and 61 dB SPL, such as 56.5 dB SPL, for the frequency band of 200 to 850 Hz. Thus, the intermediate knee point smoothly translates as the signal level evolves, when linear interpolation of the predefined kneepoint values for a frequency band is used to calculate the intermediate kneepoint for input signal level.

The pulse controller may further be configured to assign the intermediate kneepoint corresponding to the plurality of frequency bands to overlapping audio frequency ranges, thereby defining knee point for the associated electrode of the plurality of electrodes. It is understandable that the number of frequency bands and the audio frequency ranges may be same or different. It is also apparent that the more than one frequency range is covered within a single frequency band, as illustrated in the example covered in the following paragraph.

In this example, reference is made to already described look up table (Table 1 above), linearly interpolating the intermediate kneepoint and assigning the intermediate kneepoints to audio frequency range associated with the implanted electrodes. In an electrode array including 20 electrodes, each electrode has a different frequency distribution as defined by the associated audio frequency range. If electrode numbered 16 to 20 collectively cover the frequency range 200 Hz to 850 Hz, then the intermediate threshold level kneepoint for band limited audio signals relating to these electrodes for a determined total signal level of 65 dB SPL will be between 52 and 61 dB SPL, such as 56.5 dB SPL. Similarly, in another exemplary scenario, if electrode numbered 1 to 5 collectively cover the frequency range 3450 Hz to 8000 Hz, then the intermediate threshold level kneepoint for band limited audio signals relating to these electrodes for a determined total signal level of 75 dB SPL will be between 50 and 58 dB SPL, such as 54 dB SPL.

In an embodiment, the pulse controller is configured to control an incremental gain such that the incremental gain is larger for a level of the incoming signal between a lower threshold level and an intermediate threshold level, defined by the intermediate knee point, than the incremental gain for the level between the intermediate threshold level and an upper threshold level. This allows for applying a level expansion to audible signal levels below the intermediate threshold level and a level compression to comfortable signal levels above the intermediate threshold level. The purpose of the intermediate knee point is primarily to enhance information conveyed in speech and thus improve the user's ability to decode and understand speech.

In an embodiment, the processing unit may include an environment classifier that is adapted to analyse the incoming acoustic signal and determining the speech environment (quiet, medium or loud) based on determined total signal level and the predefined level associated with the different speech situations like quiet, medium or loud. The processing unit may further be configured to analyse the incoming acoustic signal and to adjust the intermediate threshold level in dependence on the analysis such that the intermediate threshold level decreases when the signal processor receives weaker incoming signals and increases when the signal processor receives louder incoming signals. Thus, the intermediate kneepoint may automatically be adjusted in accordance with the speech situation of the cochlear implant user. This results in defining automatically different incremental gains, thereby dynamically varying electrical stimulation for quiet, medium and loud environment.

The intermediate determined kneepoint defines a loudness growth function. The loudness growth function includes a first loudness growth function comprising a first incremental gain below the intermediate kneepoint and a second loudness growth function includes a second incremental gain above the intermediate kneepoint, the first incremental gain being higher than the second incremental gain. This allows for providing a level expansion and a level compression below and above the intermediate threshold level respectively. The first loudness growth function may be linear or piecewise linear between a lower kneepoint and the intermediate kneepoint. Additionally, the second loudness growth function may also be linear or piecewise linear between the intermediate kneepoint and an upper kneepoint.

In an embodiment, a smooth transition is provided in the immediate vicinity of the lower threshold level and/or the intermediate threshold level and/or upper threshold level. In other words, the lower kneepoint, the intermediate kneepoint and the upper kneepoint are preferably implemented as soft knee points, i.e. such that the incremental gain transitions smoothly in the immediate vicinity of these knee points. This assists in avoiding abrupt changes of the incremental gain at the knee points. In some embodiments, the incremental gain may be only approximately constant, for example beyond the upper threshold level kneepoint.

In an embodiment, the predefined kneepoint values and/or plurality of frequency bands and/or plurality of average signal levels in the look up table is dependent on an input provided by a user of the cochlear implant. Additionally or alternatively, the predefined kneepoint values and/or plurality of frequency bands and/or plurality of average signal levels in the look up table is statistically determined such as by utilizing a large database of speech signal from a specific language.

In another embodiment, a method for generating an electrical stimulus of a specified intensity on any audio frequency range relating to at least one electrode of a plurality of an implanted electrode array of a cochlear implant is disclosed. The method includes determining a total signal level of an incoming acoustic signal and determining, in accordance with the determined total signal level, an intermediate kneepoint for each of a plurality of frequency bands. The method also includes generating a plurality of band limited audio signals in dependence upon the incoming acoustic signal, each band limited acoustic signal representing an associated audio frequency range relating to at least one electrode of a plurality of an implanted electrode array of the cochlear implant. Lastly, the electrical stimulation signals is delivered to the plurality of electrodes of the implanted electrode array based on the generated band limited audio signals and the determined intermediate knee point corresponding to the frequency range.

In an embodiment, the determination of the total signal level is dependent upon a weighted combination, such as weighted linear combination, of incoming signal levels estimated from different beamforming modes, and the determination of the intermediate kneepoint value is based on an interpolation, such as a linear interpolation, of predefined kneepoint values for each of the plurality of frequency bands.

The method may include any of the features that are described in any of the preceding paragraphs.

BRIEF DESCRIPTION OF ACCOMPANYING FIGURES

The aspects of the disclosure may be best understood from the following detailed description taken in conjunction with the accompanying figures. The figures are schematic and simplified for clarity, and they just show details to improve the understanding of the claims, while other details are left out. The individual features of each aspect may each be combined with any or all features of the other embodiments. These and other embodiments, features and/or technical effect will be apparent from and elucidated with reference to the illustrations described hereinafter in which:

DETAILED DESCRIPTION

Figure 1A:
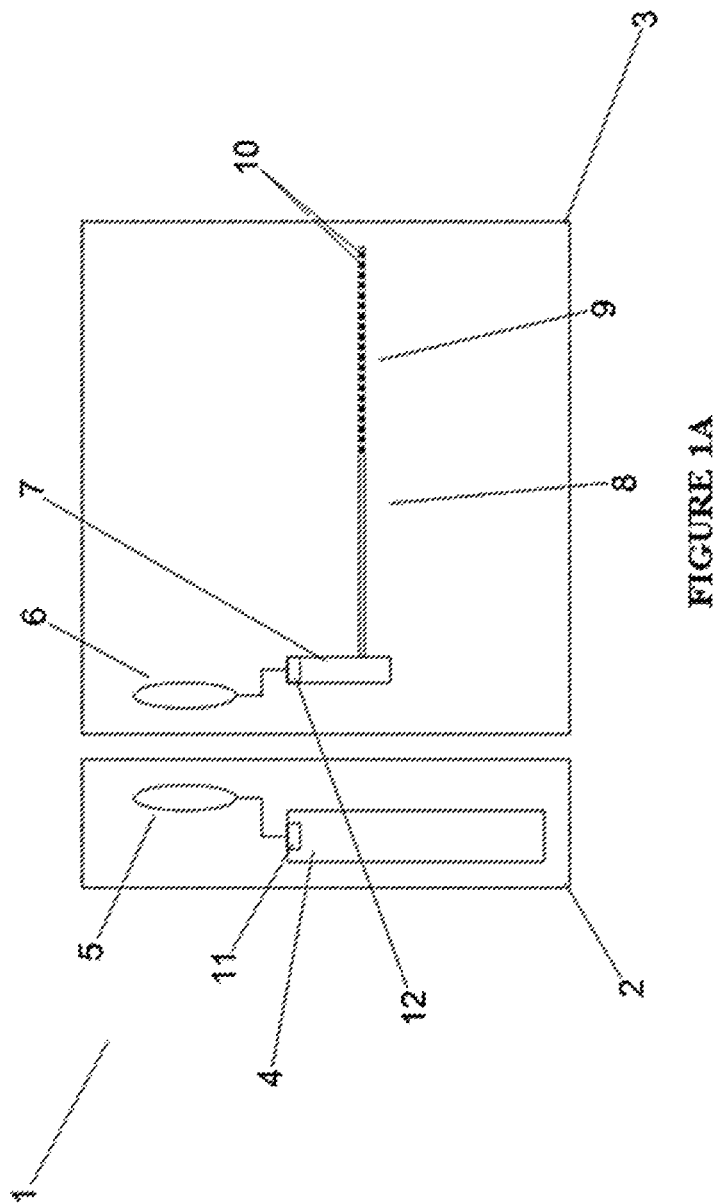
FIG. 1A illustrates a cochlear implant according to an embodiment of the disclosure.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, steps, processes, etc. (collectively referred to as "elements"). Same elements in different figures are provided with same reference numeral.

FIG. 1A illustrates a cochlear implant according to an embodiment of the disclosure. The cochlear implant includes a wearable device 2 and an implantable stimulator 3. The wearable device 2 including a pre-processor 4, a transmission coil 5 and a battery (not shown) for powering the electronic circuits of the wearable device 2 and/or the electronic circuits of the implantable stimulator 3. The implantable stimulator 3 includes a reception coil 6, a post-processor 7 and a flexible electrode carrier 8. The flexible electrode carrier 8 comprises an electrode array 9 with a plurality of electrodes 10, such as 20 electrodes. In other embodiments, the number of electrodes 10 may be different. The pre-processor 4 includes a transmitter 11, and the post-processor 7 includes a corresponding receiver 12.

The wearable device 2 is adapted to be worn on the body of the user of the cochlear implant 1, such that the pre-processor 4 may receive an acoustic signal from the user's surroundings and pre-process the acoustic signal. The transmitter 11 encodes the pre-processed signal and transmits the encoded signal to the implantable stimulator 3 by means of the transmission coil 5. The implantable stimulator 3 is adapted to be implanted in the body of the user, e.g. on the inside of the skull or in the cochlea, with the electrodes 10 adjacent to neural fibres such that electric charge pulses emitted by the electrodes 10 may stimulate these neural fibres and thus create a sensation in the user, preferably in the form of a perceived sound. The reception coil 6 is adapted to be arranged such that the post-processor 7 may receive the encoded signal from the transmitter 11 by means of the reception coil 6 and the receiver 12, decode the encoded signal by means of the receiver 12 and provide electric charge pulses to the neural fibres through the electrodes 10 of the flexible electrode carrier 8 in dependence on the decoded signal. The cochlear implant 1 may thus create sensations in the user in dependence on the incoming acoustic signal.

Figure 1B:
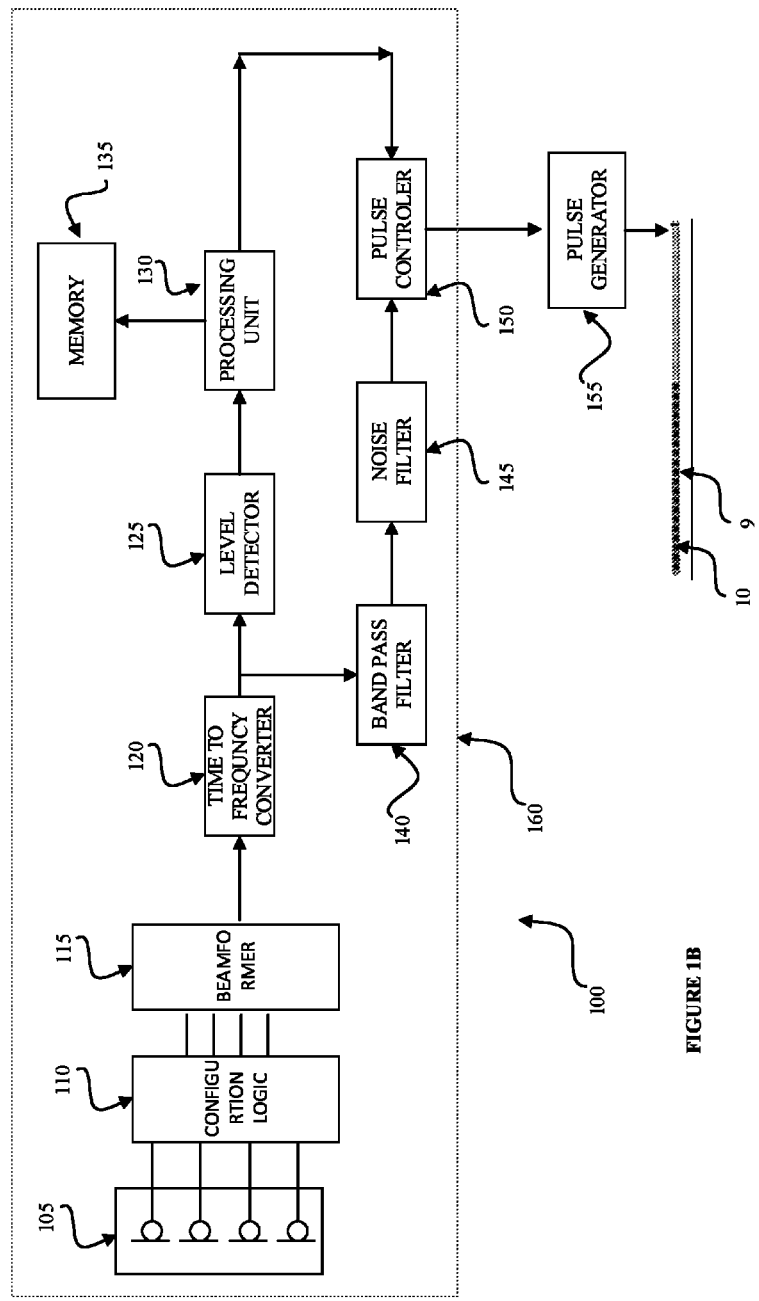
FIG. 1B illustrates a functional diagram of the cochlear implant according to an embodiment of the disclosure.

FIG. 1B illustrates a functional diagram of the cochlear implant 100 according to an embodiment of the disclosure. The implant 100 may include one or a group of microphones 105 that is configured to receive an acoustic signal from the user's surroundings and provide a corresponding electrical input signals. Although four microphones are shown, the embodiments are not limited to four microphones and any number of microphones and microphone orientations may be used in the embodiments.

The input transducers 105 are operatively coupled to a microphone configuration logic 110. The configuration logic 110 may include various front end processing, which may be applied to the outputs of the group of microphones 105 prior to performing additional, less power efficient signal processing such as noise suppression. The front end processing may include, but not limited to, electrical input signal amplification using a preamplifier, analog-to-digital conversion to digitize the amplified signal using a digitizer, pre-filtering the digitized input signal such that low and high audio frequencies are emphasized in order to achieve a frequency characteristic more like the human ear's natural frequency characteristic using a pre-emphasis filter, echo cancellation, etc. In some embodiments, the microphone configuration logic 120 may also include switch logic operatively coupled to the group of microphones 110 in order to individually turn each of the microphones on or off to configure the microphones in various ways. Additionally, in some embodiments, the microphone configuration logic 120 may be operative to receive control signals from other components to adjust frontend processing parameters.

The microphone configuration logic 110 is operatively coupled to a beamformer 115. The output of the beamformer 115 represents a microphone signal where the microphone signal is created by beamforming the outputs from one or more microphones of the group of microphones 105. The beamformer 115 may be implemented as two or more separate beamformers in order to increase the speed of operation. The beamformer receives inputs from the group of microphones 105 based on the microphone configuration logic 110 or by selecting microphone outputs as needed for given beamform patterns. The beamformer 115 may be adaptive beamformers that are operative to determine the magnitude and phase coefficients needed to combine microphone outputs of the group of microphones 110 in order to steer a beam or a null in a desired direction.

The beamformer 115 may be operatively connected to a time-to-frequency domain converter 120, which is configured to transform the incoming acoustic signal or the output of the beamformer 115 from a time-domain representation to a frequency-domain representation with each of the band limited audio signal representing an audio frequency range/channel. The number of frequency channels preferably equals the maximum number of auditory channels that may be stimulated by the electrodes 10 of the electrode array 9. The signal level detector 125 is configured to determine a total signal level of the incoming acoustic signal. The total signal level is determined by estimating signal levels obtained from at least one beamforming mode. In case there are more than one beamforming modes are used typically in parallel, then the total signal level is determined by performing weighted combination, such as weighted linear combination, of the estimated signal levels obtained from different beamforming modes. The processing unit 130 is receives the determined total signal value from the level detector 125 and access the stored look up table from a memory 135 and based on an interpolation, as described in earlier sections, determines the intermediate kneepoint for each of a plurality of frequency band.

A band pass filter 140 processes the signal received after the time-to-frequency converter and generates to a band-limited audio signals, each of the band limited audio signal representing an audio frequency range/channel. The number of frequency channels preferably equals the maximum number of auditory channels that may be stimulated by the electrodes 10 of the electrode array 9.

The noise filter 145 attenuates undesired signal components in the band-limited audio signals and provides corresponding noise-filtered signals. Preferably, one noise-filtered signal is provided for each frequency channel, defined by the audio frequency range, and thus for each band-limited audio signal. Preferably, the pulse controller 150 causes the pulse generator 155 to provide one stream of electric charge pulses for each noise-filtered signal. The pulse controller 150 computes emission times for the electric charge pulses. In other embodiments, alternative time schemes may be used as is well known in the art.

The pulse controller 150 further computes target charge amounts E for the individual electric charge pulses in dependence on the noise-filtered signals and the determined intermediate kneepoint, as received from the processing unit 130. Thus, the pulse controller is configured to deliver electrical stimulation signals to the plurality of electrodes of the implanted electrode array based on the generated band limited audio signals and the determined intermediate knee point corresponding to the frequency range. This is achieved by configuring the pulse controller 150 to assign the intermediate kneepoint corresponding to the plurality of frequency bands to overlapping audio frequency ranges, thereby defining knee point for the associated electrode of the plurality of electrodes. The computation of the target charge amounts E along with intermediate kneepoint is explained in detail in earlier sections and in the description of FIGS. 3 and 4 below.

The pulse generator 155 generates electric charge pulses and provides the electric charge pulses to the electrodes 10 of the electrode array 9 implanted in the cochlea, such that the emitted electric charge in each pulse corresponds to the respective target charge amount E. The pulse generator 24 preferably provides each electric charge pulse as a current flowing out through one or more electrodes 10, those electrodes 10 thus having positive polarity, and back through one or more other electrodes 10, those electrodes 10 thus having negative polarity, thereby causing the current to flow from the positive electrodes 10 to the negative electrodes 10 through the tissue and thereby stimulating neural fibres in or adjacent to the tissue.

The different elements illustrated here may be included in a signal processor 160 of the cochlear implant. It is understandable that an element may be configured to integrate the functionalities of some other element of the signal processor. For example, the functionality of the pulse controller 150 may be integrate in the processing unit 130.

Figure 2:
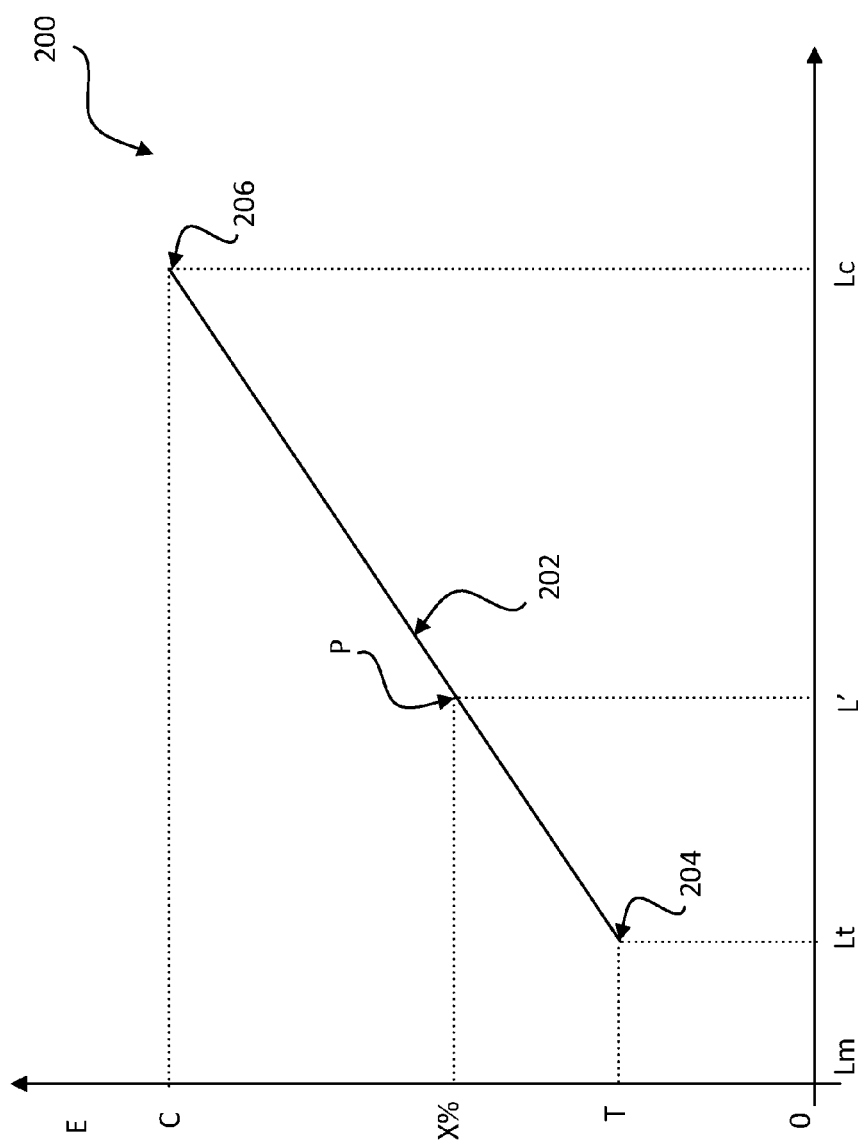
FIG. 2 illustrates a mapping function for mapping signal level to electrical stimulation levels.

FIG. 2 illustrates a mapping function 200 for mapping signal level to electrical stimulation levels. The mapping illustrates how target charge amount E for the individual electric charge pulses in each pulse stream or auditory channel may be computed from the input levels L (dB SPL) of the respective typically noise-filtered signal using a linear mapping function. The L axis and the E axis are both linear, and the mapping function 202 maps the logarithm L of the sound pressure or the energy in the respective noise-filtered signal into a target charge amount E (stimulation percentage) for the respective pulse stream or auditory channel. As an example, for a specific audio frequency range of an auditory channel, at level L', the target charge amount is x %. The mapping functions may differ between the auditory channels due to different coupling between the electrodes of the electrode array and the neural fibres and/or different sensitivity in the different neural fibres.

A normal-hearing person has a frequency-dependent hearing threshold that defines the weakest sounds the person can hear, as defined by the lower threshold level kneepoint 204 that corresponds to level Lt and target charge amount T usually 0%. A frequency-dependent uncomfortable level (UCL) that defines the weakest sounds that cause discomfort in the person, as defined by upper threshold level kneepoint 206 that corresponds to the level Lc and target charge amount C usually 100%. In the following text, the term "comfortable acoustic range" refers to the frequency-dependent level range between the typical hearing threshold and the typical UCL for normal-hearing persons. Statistically obtained values for these levels are well known in the art. It is also well known that normal-hearing persons typically perceive loudness approximately logarithmic within the comfortable acoustic range.

Figure 3:
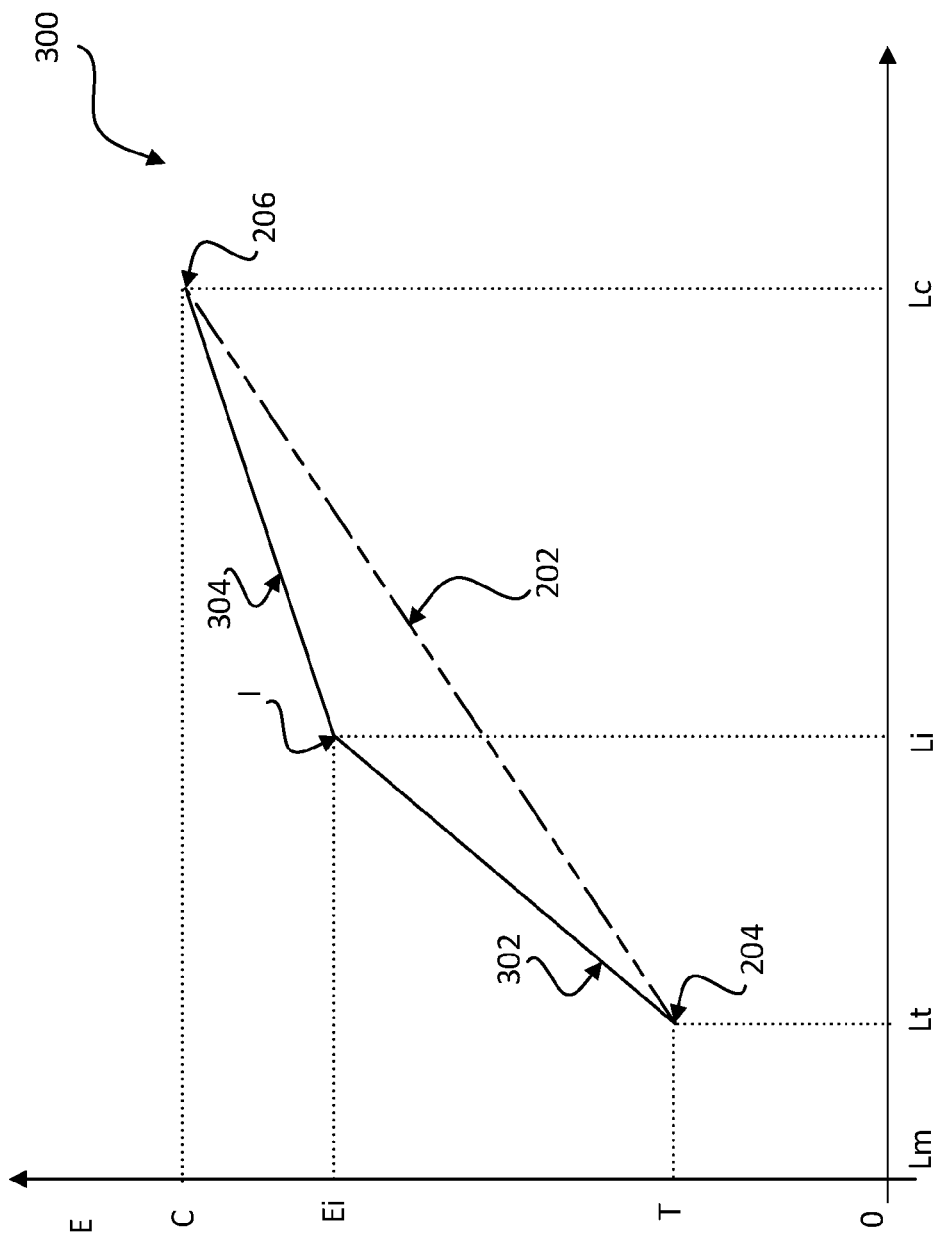
FIG. 3 illustrates an enhanced mapping function with an intermediate kneepoint according to an embodiment of the disclosure.

FIG. 3 illustrates an enhanced mapping function with an intermediate kneepoint according to an embodiment of the disclosure. The mapping function 200 defines the mapping function as defined in the FIG. 2. The enhanced mapping 300 deviates from the mapping function only in that it extends from the lower knee point 204 to the upper knee point 206 via an intermediate knee point I, such that the incremental gain $G_i$ is larger between the lower knee point 204 and the intermediate knee point I as indicated by the first loudness growth function 302 than the incremental gain Gi between the intermediate knee point I and the upper knee point 206 as indicated by the second loudness growth function 304. In other words, the incremental gain $(Ei-T)/(Li-Lt)$ is greater than the incremental gain $(C-Ei)/(Lc-Li)$.

At the intermediate knee point I, the enhanced mapping function maps an intermediate threshold level Li to an intermediate charge Ei. The intermediate charge Ei may be determined such that it is located at a distance from the threshold charge T. For example, Ei may be about 60%, about 70%, about 80% or about 90% of the distance between the threshold charge T and the maximum comfortable charge C. The determination of the intermediate charge Ei may further be based on preferences of the user and/or on knowledge about the user's hearing ability in general.

Compared to the mapping function 200, the enhanced mapping function 300 thus applies a level expansion to audible signal levels L below the intermediate threshold level $L_i$ and a level compression to comfortable signal levels L above the intermediate threshold level $L_i$. The purpose of the intermediate knee point I is primarily to enhance information conveyed in speech and thus improve the user's ability to decode and understand speech.

As described earlier, the intermediate kneepoint is determined by interpolating predefined kneepoint values, available from a look up table, for each of the plurality of frequency bands. This allows for automatic determination of the intermediate knee point based on the user's environment. The intermediate charge Ei is preferably closer to the maximum comfortable charge C than to the threshold charge T.

In an embodiment, the cochlear implant 1 may also include a user-operable control (not shown), such as a control element on the wearable device 2 and/or on a wired or wireless remote control, that allows the user to adjust the intermediate threshold level Li. The user-operable control allows the user to adjust the intermediate threshold level Li in predefined level steps, such as e.g. 10 dB steps or 6 dB steps. This allows the user to adapt the cochlear implant to weaker and/or louder speech.

In an embodiment, the cochlear implant may also include a user-operable control (not shown) that allows the user to switch the hearing device between using the mapping function 200 and the enhanced mapping function 300 for relevant auditory channels. This allows the user to adapt the signal processing in the cochlear implant to situations with and without speech. Thus, when speech is present, the user may choose signal processing that enhances speech, and when speech is absent, the user may choose signal processing that provides a more natural loudness curve, e.g. for environmental sounds. The cochlear implant may preferably include a speech detector that detects speech in the acoustic signal and switches to using the enhanced mapping function 300 for the relevant auditory channels when detecting speech and switches to using the mapping function 200 when speech is absent, thus automatically performing switching otherwise made by the user.

Figure 4:
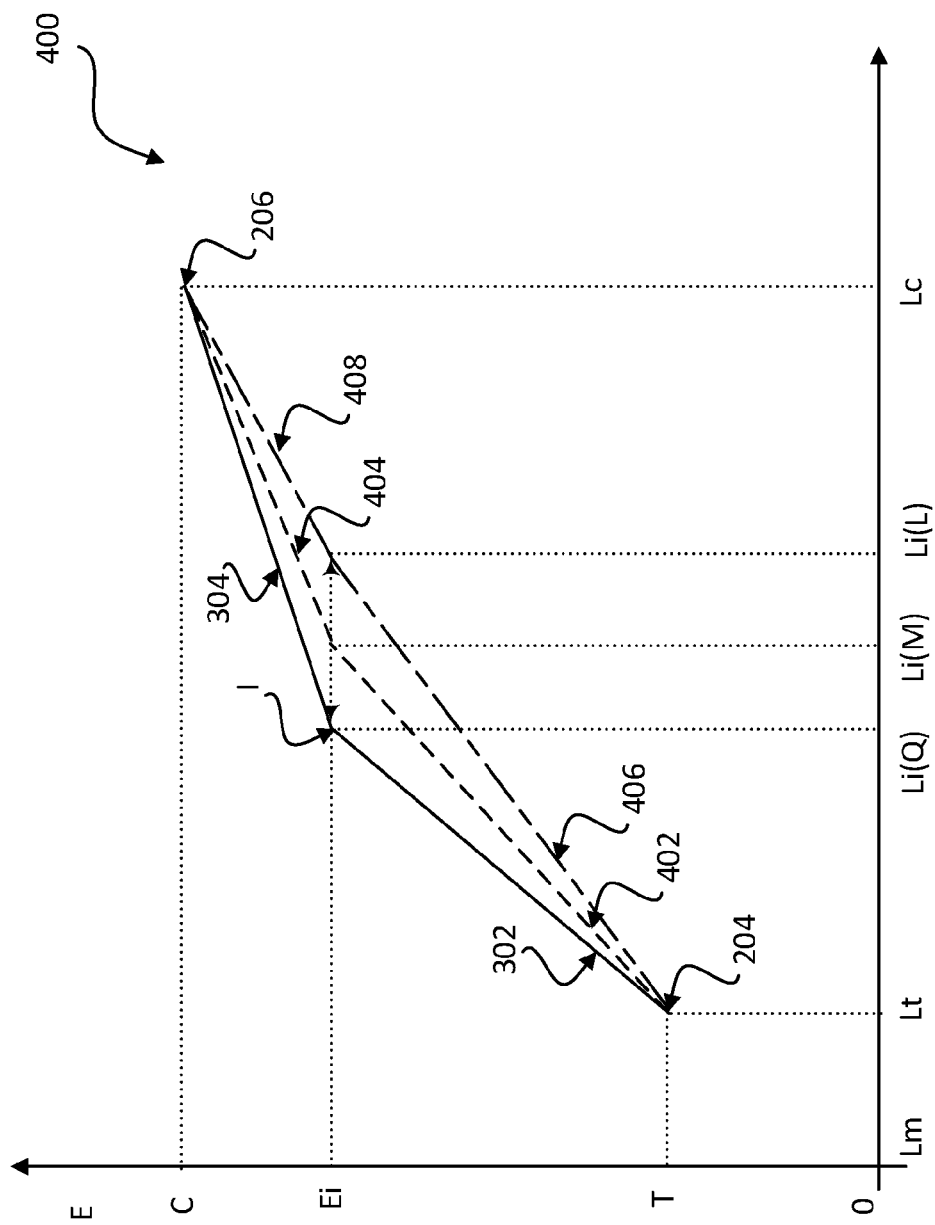
FIG. 4 illustrates an enhanced mapping function for different sound situations according to an embodiment of the disclosure.

FIG. 4 illustrates an enhanced mapping function 400 for different speech situations according to an embodiment of the disclosure. The cochlear implant may preferably comprise an environment classifier (not shown) that analyses the incoming acoustic signal and adjusts the intermediate threshold level $L_i$ in dependence on the analysis, such that the intermediate threshold level Li decreases when weaker speech signals are received and increases when louder speech signals are received. The environment classifier receives the determined total signal level and compares it with the situation specific speech levels defined in the look up table in order to determine whether the user's sound environment is quiet, medium or loud. Thereafter, for specific frequency band in a the determined sound environment, the intermediate kneepoint is calculated based on the interpolation. In an embodiment, the processing unit may be configured to perform the function of the environment classifier.

Referring back to Table 1—it is apparent that for a specific frequency band, the intermediate kneepoint for quiet environment is at a lower intermediate threshold level than for the medium environment, which has a lower intermediate threshold level when compared with that of the loud environment. In other words, the intermediate threshold level is adjusted in dependence on the determination of the sound situation such that the intermediate threshold level decreases when the signal processor receives weaker incoming signals and increases when the signal processor receives louder incoming signals. This is illustrated by the mapping function 302-304 having the intermediate threshold level Li(Q) for the quiet sound situation environment, the mapping function 402-404 having the intermediate threshold level Li(M) for the medium sound situation environment, and the mapping function 406-408 having the intermediate threshold level Li(L) for the loud sound situation environment.

In an embodiment, the incremental gain between the lower kneepoint and the intermediate kneepoint for quiet sound situation environment is higher than that for the medium sound situation environment, which has higher incremental gain than that for the loud sound situation environment. This is apparent from $(Ei-T)/(Li(Q)-Lt)>(Ei-T)/(Li(M)-Lt)>(Ei-T)/(Li(L)-Lt)$.

The pulse controller may further be configured to assign the intermediate kneepoint corresponding to the plurality of frequency bands to overlapping audio frequency ranges, thereby defining knee point for the associated electrode of the plurality of electrodes. In this example, reference is made to already described look up table (Table 1 above), linearly interpolating the intermediate kneepoint and assigning the intermediate kneepoints to audio frequency range associated with the implanted electrodes. In an electrode array including 20 electrodes, each electrode has a different frequency distribution as defined by the associated audio frequency range. If electrode numbered 16 to 20 collectively cover the frequency range 200 Hz to 850 Hz, then the intermediate threshold level kneepoint for band limited audio signals relating to these electrodes for a determined total signal level of 65 dB SPL will be between 52 and 61 dB SPL, such as 56.5 dB SPL.

The disclosure thus describes that using frequency band specific predefined kneepoint values to automatically determine intermediate kneepoints for different user environment as determined based on the total incoming signal level; it is possible to automatically adapt incremental gain and determine electrical stimulation amount for different frequency channel in the cochlear implant.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification do not preclude the presence or addition of one or more other features, steps, operations, elements, components, and/or groups thereof. It will also be understood that when an element is referred to as being "connected" or "coupled" to another element, it can be directly connected but other intervening elements may also be present, unless expressly stated otherwise. As used herein, the term "and/or" includes any and all combinations of one or more of the associated listed items.

It should be appreciated that recited particular features, structures or characteristics in different embodiments may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

I claim:

1. A cochlear implant comprising
a signal level detector configured to determine a total signal level of an incoming acoustic signal;
a processing unit configured to determine, in accordance with the determined total signal level, an intermediate knee point in a mapping function for one or more frequency bands, wherein the mapping function outputs a charge amount corresponding to a signal level inputted to the mapping function;
a bandpass filters configured to generate a plurality of band limited audio signals in dependence upon the incoming acoustic signal, each band limited audio signal representing an associated audio frequency range relating to at least one electrode of a plurality of an implantable electrode array of the cochlear implant; and a pulse controller configured to directly map one or more generated band limited audio signals into a stream of target charge amounts by inputting the signal levels of each of the one or more generated band limited audio signals to the mapping function including the intermediate knee point determined for the corresponding frequency range, and obtaining the corresponding charge amounts outputted by the mapping function as the target charge amounts, and deliver electrical stimulation signals to the plurality of electrodes of the implantable electrode array by generating electric charge pulses corresponding to the stream of target charge amounts which are outputted by the mapping function in response to the inputted signal levels of the one or more generated band limited audio signals that are directly mapped, wherein the intermediate knee point defines within the mapping function a loudness growth function comprising a first loudness growth function comprising a first incremental gain below the intermediate knee point and a second loudness growth function comprising a second incremental gain above the intermediate knee point, the first incremental gain being higher than the second incremental gain, and wherein the mapping function maps the one or more generated band limited audio signals in units of decibels of sound pressure level (dB SPL) into the stream of target charge amounts defined as a percentage of a maximum comfort charge.

2. The cochlear implant according to claim 1, wherein the signal level detector is configured to determine the total signal level by estimating signal levels obtained from at least one beamforming mode; or determine the total signal level by performing weighted combination of the estimated signal levels obtained from different beamforming modes if more than one beamforming mode is used.

3. The cochlear implant according to claim 1, wherein the processing unit is configured to determine the intermediate knee point by interpolating predefined kneepoint values for the one or more frequency bands.

4. The cochlear implant according to claim 1, wherein the processing unit is configured to determine the intermediate knee point by accessing a look up table comprising predefined knee point values corresponding to the one or more frequency bands and a plurality of average signal levels.

5. The cochlear implant according to claim 1, wherein the pulse controller is configured to assign the intermediate kneepoint corresponding to the one or more frequency bands to overlapping audio frequency ranges, thereby defining a knee point for the associated electrode of the plurality of electrodes.

6. The cochlear implant according to claim 1, wherein the pulse controller is configured to control an incremental gain such that the incremental gain is larger for a level of the incoming signal between a lower threshold level and an intermediate threshold level, defined by the intermediate knee point, than the incremental gain for the level between the intermediate threshold level and an upper threshold level.

7. The cochlear implant according to claim 6, wherein, in the mapping function, the gain transitions incrementally in the immediate vicinity of the lower threshold level and/or the intermediate threshold level and/or upper threshold level.

8. The cochlear implant according to claim 1, wherein the processing unit is further configured to analyse the incoming acoustic signal and to adjust the intermediate threshold level in dependence on the analysis such that the intermediate threshold level decreases when the signal processor receives weaker incoming signals and increases when the signal processor receives louder incoming signals.

9. The cochlear implant according to claim 1, wherein
the first loudness growth function is linear or piecewise linear between a lower kneepoint and the intermediate kneepoint; and/or
the second loudness growth function is linear or piecewise linear between the intermediate kneepoint and an upper kneepoint.

10. The cochlear implant according to claim 1, wherein the predefined kneepoint values and/or the one or more frequency bands and/or the plurality of average signal levels in the look up table is dependent on a statistical determination and/or an input provided by a user of the cochlear implant.

11. The cochlear implant according to claim 1, further comprising an input transducer configured to receive the incoming acoustic signal and to provide a corresponding electric input signal; and a digitiser adapted to digitise the electric input signal and to provide the digitised signal as the input audio signal to the signal level detector for determining the total signal level.

12. A method for generating an electrical stimulus of a specified intensity on any audio frequency range relating to at least one electrode of a plurality of an implanted electrode array of a cochlear implant, the method comprising determining a total signal level of an incoming acoustic signal;

determining, in accordance with the determined total signal level, an intermediate knee point in a mapping function for one or more frequency bands, wherein the mapping function outputs a charge amount corresponding to a signal level inputted to the mapping function;

generating a plurality of band limited audio signals in dependence upon the incoming acoustic signal, each band limited acoustic signal representing an associated audio frequency range relating to at least one of a plurality of electrodes of an implantable electrode array of the cochlear implant;

directly map one or more generated band limited audio signals into a stream of target charge amounts by inputting the signal levels of each of the one or more generated band limited audio signals to the mapping function including the intermediate knee point determined for the corresponding frequency range, and obtaining the corresponding charge amounts outputted by the mapping function as the target charge amounts, and delivering electrical stimulation signals to the plurality of electrodes of the implantable electrode array by generating electric charge pulses corresponding to the stream of target charge amounts which are outputted by the mapping function in response to the inputted signal levels of the one or more generated band limited audio signals that are directly mapped, wherein the intermediate knee point defines within the mapping function a loudness growth function comprising a first loudness growth function comprising a first incremental gain below the intermediate knee point and a second loudness growth function comprising a second incremental gain above the intermediate knee point, the first incremental gain being higher than the second incremental gain, and wherein the mapping function maps the one or more generated band limited audio signals in units of decibels of sound pressure level (dB SPL) into the stream of target charge amounts defined as a percentage of a maximum comfort charge.

13. The method according to claim 12, wherein the determination of the total signal level is dependent upon a weighted combination of incoming signal levels estimated obtained from different beamforming modes, and the determination of the intermediate kneepoint value is based on an interpolation of predefined kneepoint values for the one or more frequency bands.

14. The method according to claim 12, wherein the intermediate knee point is determined by accessing a look up table comprising predefined knee point values corresponding to the one or more frequency bands and a plurality of average signal levels.

15. The method according to claim 12, further comprising assigning the intermediate kneepoint corresponding to the one or more frequency bands to overlapping audio frequency ranges, thereby defining a knee point for the associated electrode of the plurality of electrodes.

16. The method according to claim 12, further comprising controlling an incremental gain such that the incremental gain is larger for a level of the incoming signal between a lower threshold level and an intermediate threshold level, defined by the intermediate knee point, than the incremental gain for the level between the intermediate threshold level and an upper threshold level.

17. The method according to claim 16, wherein, in the mapping function, the gain transitions incrementally in the immediate vicinity of the lower threshold level and/or the intermediate threshold level and/or upper threshold level.

18. The method according to claim 12, further comprising signaling the incoming acoustic signal and adjusting the intermediate threshold level in dependence on the analysis such that the intermediate threshold level decreases when the signal processor receives weaker incoming signals and increases when the signal processor receives louder incoming signals.

* * * * *